United States Patent
Farber

(10) Patent No.: US 11,235,061 B1
(45) Date of Patent: Feb. 1, 2022

(54) TOPICAL SOLUBILIZED IVERMECTIN FOR INFLAMMATORY SKIN CONDITIONS

(71) Applicant: MOUNTAIN VALLEY MD INC., Vaughan (CA)

(72) Inventor: Michael Farber, Livingston, NJ (US)

(73) Assignee: MOUNTAIN VALLEY MD INC., Vaughan (CA)

( * ) Notice: Subject to any disclaimer, the term of this patent is extended or adjusted under 35 U.S.C. 154(b) by 0 days.

(21) Appl. No.: 17/228,077

(22) Filed: Apr. 12, 2021

(51) Int. Cl.
| | | |
|---|---|---|
| *A61K 36/00* | (2006.01) | |
| *A61K 47/61* | (2017.01) | |
| *A61K 9/00* | (2006.01) | |
| *A61K 47/26* | (2006.01) | |
| *A61K 31/573* | (2006.01) | |
| *A61K 9/06* | (2006.01) | |
| *A61K 36/889* | (2006.01) | |
| *A61K 47/22* | (2006.01) | |
| *A61K 36/886* | (2006.01) | |
| *A61K 47/46* | (2006.01) | |

(52) U.S. Cl.
CPC ............ *A61K 47/61* (2017.08); *A61K 9/0014* (2013.01); *A61K 9/06* (2013.01); *A61K 31/573* (2013.01); *A61K 36/886* (2013.01); *A61K 36/889* (2013.01); *A61K 47/22* (2013.01); *A61K 47/26* (2013.01); *A61K 47/46* (2013.01)

(58) Field of Classification Search
CPC ..... A61K 9/0014; A61K 47/46; A61K 36/886
See application file for complete search history.

(56) References Cited

U.S. PATENT DOCUMENTS

| | | | | |
|---|---|---|---|---|
| 2011/0319805 | A1* | 12/2011 | Morris | A61P 17/00 602/48 |
| 2016/0250244 | A1* | 9/2016 | Forget | A61P 33/10 514/30 |
| 2018/0028547 | A1* | 2/2018 | Kerob | A61K 31/4184 |

FOREIGN PATENT DOCUMENTS

CN 104208017 A * 12/2014

\* cited by examiner

*Primary Examiner* — Qiuwen Mi
(74) *Attorney, Agent, or Firm* — Michael J. Feigin, Esq.; Feigin and Fridman LLC

(57) ABSTRACT

A topical solubilized ivermectin pharmaceutical composition for the treatment and/or prevention of inflammatory skin conditions is disclosed herein. The topical solubilized ivermectin pharmaceutical composition comprises an ivermectin and a cyclodextrin. Particularly, ivermectin is combined with cyclodextrin to form an ivermectin-cyclodextrin complex solubilized in a Tween80-water solution up to a 30% by weight of solution. The present invention features a formulation of Ivermectin-cyclodextrin complex solubilized in a Tween80-water solution incorporated into lotion or cream or gel base that is highly effective in the treatment inflammatory skin conditions at a concentration of, in some embodiments, 0.125% to 5% ivermectin by weight.

12 Claims, No Drawings

TOPICAL SOLUBILIZED IVERMECTIN FOR INFLAMMATORY SKIN CONDITIONS

FIELD OF THE DISCLOSED TECHNOLOGY

The present invention relates to a formulation of ivermectin-cyclodextrin complex into topical pharmaceutical compositions useful for the treatment of inflammatory skin conditions. More particularly, the present invention also relates to a topical solubilized ivermectin pharmaceutical composition suited for administration to humans.

BACKGROUND

Inflammatory skin conditions occur when a layer of the skin becomes inflamed due to the recognition of a foreign element by the immune system. In response the immune system begins to generate antibodies.

Moreover, inflammation is a response to stimulus that occurs in our body when our body recognizes a foreign invader such as infectious viruses and bacteria which are recognized by our immune system. A response is sent to fight against the dangerous pathogens and begin the healing process. Furthermore, our body is designed in such a way that it also sends a response in order to promote healing and recovery when we encounter a wound or area of damaged tissue. Skin inflammation usually occurs as a rash that may be raised, red, or warm. Some inflammatory rashes cause blisters or pimples, and some may burn, sting, or itch.

Moreover, the common causes of skin inflammation are infection, immune system dysfunction, allergic reaction, gut condition, photosensitivity, and injury or wound. Infection includes bacterial, fungal and viral infections which causes skin inflammation. Some of the most common bacterial skin infections include cellulitis and staph infections. Furthermore, some common viral infections include warts and herpes simplex, and common fungal infections include ringworm and athlete's foot. Additionally, seborrheic dermatitis is a chronic skin condition that causes red, scaly skin patches and dandruff and is caused by yeast that resides in the oil on the skin. A second cause of skin inflammation is immune system dysfunction in which the immune system does not function properly and causes immune cells to mistakenly attack our body's own healthy cells, for example in psoriasis. A third cause of skin inflammation is an allergic reaction. An allergic reaction occurs if your immune system overreacts when it senses a foreign substance and sends cells to attack the invader. Foods, medications, and pollen can all trigger allergic reactions and cause skin redness, hives, and inflammation. A fourth cause of skin inflammation is gut condition in which gut conditions and an imbalanced gut microbiome are linked to skin inflammation and chronic inflammatory skin conditions. A fifth cause of skin inflammation is photosensitivity. Photosensitivity is an extreme sensitivity to sunlight that can trigger an immune system response. A photosensitive reaction can be induced by spending time in the sun while taking certain medications, including some antibiotics and diuretics. Photosensitive skin becomes red, inflamed, and burned after only minimal UV radiation exposure. A sixth cause of skin inflammation is injury or wound. Cuts, scrapes, burns, and surgical wounds cause redness, swelling, and warmth at the site of the injury. The immune system sends an inflammatory response to help heal damaged tissue.

Various pharmaceutical preparations have been used for the treatment and prevention of inflammatory skin conditions, including skin cleansing compositions, antibacterial compositions, anti-inflammatory compositions and dermatological compositions. However, the compositions provided in the prior arts involve the use of alcohol and propylene glycol which cause skin irritations. An object of the invention is to provide compositions which overcome such prior art problems. "Irritating" is defined as "producing a visibly noticeable immune response or inflammation." "Non-irritating" is defined as "the absence of the production of a visibly noticeable immune response or inflammation."

Discussing a different aspect of the prior art, Ivermectin is a mixture of two compounds belonging to the avermectin class, 5-O-demethyl-22,23-dihydroavermectin A1a and 5-O-demethyl-22,23-dihydroavermectin A1b. They are also known as 22,23-dihydroavermectin B1a and 22-23-dihydroavermectin B1b. Ivermectin comprises at least 80% of 22,23-dihydroavermectin B1a and less than 20% of 22,23-dihydroavermectin B1b. This active agent is part of the avermectin class, a group of macrocyclic lactones produced by the bacterium *Streptomyces avermitilis* (Reynolds J E F (Ed) (1993) Martindale). The extra pharmacopoeia, 29th Edition, Pharmaceutical Press, London).

In the middle of the 1980s, ivermectin was presented as a broad-spectrum anti-parasitic medicinal product for veterinary use (W. C. CAMPBELL, et al., (1983). Ivermectin: a potent new anti-parasitic agent, Science, 221, 823-828). It is effective against most common intestinal worms (except tapeworms), most acarids and some lice. It in particular exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependent chloride channels, such as those involving the neuromediator GABA (gamma-aminobutyric acid).

Ivermectin is more particularly an anthelmintic. It has already been described in humans in the treatment of river blindness caused by *Onchocerca volvulus*, of gastrointestinal strongyloidiasis (anguillulosis) (product Stromectol®), and of human scabies (Meinking T L et al., N. Engl. J. Med., 1995 Jul. 6; 333(1):26-30, "The treatment of scabies with ivermectin") and also in the treatment of microfilaraemia diagnoses or suspected in individuals suffering from lymphatic filariasis due to *Wuchereria bancrofti*.

Ivermectin along with cyclodextrin in specific concentration can lead to solve the problem of prior arts. Cyclodextrins are a family of cyclic oligosaccharides, consisting of a macrocyclic ring of glucose subunits joined by α-1,4 glycosidic bonds. Cyclodextrins are produced from starch by enzymatic conversion. Furthermore, cyclodextrins have shown to enhance absorption into the skin by 20 times or more and hence can be used to form a complex with solubilized ivermectin in order to prevent or treat inflammatory skin conditions.

Ivermectin has been successfully used for the treatment of dermatological conditions such as rosacea however the formulations that are used have alcohols such as propylene glycol and exhibit adverse events such as painful sensation, dry, itchy, irritated skin to an extent of approximately 20% such that there is need for an improved delivery system of ivermectin for the treatment of inflammatory skin diseases.

A number of solutions were introduced in order to solve the abovementioned problems. In one of the closest relevant arts, U.S. Pat. No. 8,815,816 discloses that dermatological conditions/afflictions such as rosacea, common acne, seborrheic dermatitis, perioral dermatitis, acneform rashes, transient acantholytic dermatosis, and acne necrotica miliaris, most notably rosacea, are treated by topically applying onto the affected skin area of an individual in need of such treatment, a topical pharmaceutical composition which comprises ivermectin. Moreover, Ivermectin has been successfully used for the treatment of dermatological conditions such as rosacea however the formulations that are used comprise alcohols such as propylene glycol and exhibit adverse events such as painful sensation, dry, itchy, irritated skin to an extend of approximately 20% such that there is need for an improved delivery system of ivermectin for the treatment of inflammatory skin diseases.

Another relevant art, U.S. Pat. No. 6,133,310 discloses the use of ivermectin topically in the form of a prototype of a lotion consisting of a mixture of ivermectin and water, and also mentions the possibility of a prototype of a cream consisting, for its part, of a mixture of ivermectin and an excipient such as propylene glycol or sodium lauryl sulfate but describes no pharmaceutical composition as such. These mixtures are similar to experimental preparations used in the context of initial results of proof of concept. In fact, the elements disclosed in that patent provide no teaching to those skilled in the art regarding the feasibility of industrially acceptable pharmaceutical compositions containing ivermectin, in particular having good cosmetic properties and a shelf-life which is sufficiently long for an industrial pharmaceutical product (minimum of 2 years).

Another relevant prior art reference, U.S. Pat. No. 6,673,374 discloses a pharmaceutical composition and methods for treating inflammatory skin conditions. The compositions include hydrogen peroxide, one or more moisturizing agents, and an anti-inflammatory agent. The pharmaceutical compositions may optionally include one or more exfoliants. The compositions can be used to treat inflammatory skin conditions such as dermatitis, including, but not limited to seborrheic dermatitis, nummular dermatitis, contact dermatitis, atopic dermatitis, exfoliative dermatitis, perioral dermatitis, and stasis dermatitis; psoriasis; folliculitis; rosacea; acne; impetigo; erysipelas; paronychia, erythrasma; and eczema.

The prior art described above, indicate that some studies have been carried out to treat inflammatory skin conditions. There still remains a need to develop a composition which is free from alcohol and propylene glycol which are skin irritants. Moreover, it is required that the composition utilizes 100% pure organic materials and is free from harmful chemicals. Furthermore, there is a need to utilize solubilized ivermectin cyclodextrin complex for the treatment of inflammatory skin conditions.

Hence, there remains a greater need for effective complex of ivermectin and cyclodextrin to maximize the anti-inflammatory effects of ivermectin and cyclodextrin that has been solved by present instant invention.

All the problems, disadvantages and the limitations of the above-mentioned relevant and conventional arts are being overcome by the method and composition of the present instant invention, which has various technical advancements and certainly economic benefits over the conventional arts.

SUMMARY OF THE INVENTION

The presently disclosed technology solves the above-mentioned problems and discloses a topical solubilized ivermectin pharmaceutical composition for inflammatory skin conditions. The pharmaceutical composition disclosed herein is formulated in a manner that produces an ivermectin complexed with a cyclodextrin usable for topical treatment of skin while preventing and/or substantively healing an inflammatory skin condition. An "inflammatory skin condition" is defined as a noticeable, to the naked eye, rash, heat, or blistering.

An objective of the present invention is to provide a much needed and highly effective topical ivermectin pharmaceutical composition useful for the treatment of inflammatory skin conditions.

The present instant invention provides a topical ivermectin pharmaceutical composition discloses herein for the treatment of inflammatory skin conditions.

In one aspect of the present invention, the invention provides an ivermectin in a 0.125% to 5% (w/w) concentration and a cyclodextrin. Further, the ivermectin is combined with the cyclodextrin to form an ivermectin-cyclodextrin complex which is solubilized in a Tween80-water solution at a maximum of 30% by weight of solution.

In another embodiment, the ivermectin according to the invention consists of at least 80% of 22,23-dihydroavermectin B1a and less than 20% of 22,23-dihydroavermectin B1b.

In yet another embodiment, the present invention provides the composition is formulated for topical administration on the infected area of the skin.

In yet another embodiment, the composition for topical administration on the infected area of the skin in an anhydrous form.

In yet another embodiment, the present invention provides the composition is formulated for the treatment and/or prevention of inflammatory skin conditions.

In yet another embodiment, the present invention provides the composition for inflammatory skin conditions such as Dermatitis, Psoriasis, and Eczema.

In another embodiment, the composition according to the invention is suited for treating the skin and is in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases.

Moreover in another embodiment, the composition according to the invention is in the form of suspensions of microspheres or nanospheres or of lipid or polymeric vesicles or of polymeric patches and of hydrogels for controlled release.

In another embodiment, the composition according to the invention is in the form of a cream or a lotion type, or a gel, or a solution.

In another embodiment, the composition according to the invention is a simple gel such as aloe vera gel.

In another embodiment, the solubilized Ivermectin cyclodextrin complex at pH 6.4 is combined into the aloe vera gel for direct application to the surface of the skin.

In another embodiment, the gel, cream and/or lotion is free from irritants such as parabens, methylparabens, phthalates and all other agents and preservatives that elicit allergenic or immunogenic reactions.

Moreover in another embodiment, the ivermectin-cyclodextrin complex is effectively dispersed within said cream, gel or lotion or combined with creams such as hydrocortisone creams.

In another embodiment, the ivermectin-cyclodextrin complex is non-irritating to the inflamed skin.

In another embodiment, the effective dose of the ivermectin on a w/w basis is from 0.125% to 5% and in some embodiments, from 0.125% to 5% of the weight of said cream, lotion or gel.

In yet another embodiment, the composition utilizes 100% organic materials such as sunflower oil, aloe vera, coconut oil, oat/milk and/or vitamin E cream base.

Other features and advantages of the present instant invention will be apparent from the detailed description, and from the appended claims. Thus, other aspects of the present instant invention are described in the following disclosure and are within the ambit of the present instant invention.

DESCRIPTION OF EMBODIMENTS OF THE DISCLOSED TECHNOLOGY

In the following description, certain specific details are set forth in order to provide a thorough understanding of various embodiments of the present instant invention. However, one skilled in the art will understand that the invention is not limited to the embodiments described herein, and are not intended to represent the scale of the various embodiments. It should be understood that the detailed description are not intended to limit the invention to the particular form disclosed, but on the contrary, the invention is to cover all modifications, equivalents, and alternatives falling within the scope of the present instant invention as defined by the appended claims. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned.

In this specification, whenever a composition or an element or a group of elements is preceded with the transitional phrase "comprising", it is understood that we also contemplate the same composition, element or group of elements with transitional phrases "consisting of", "consisting", "selected from the group of consisting of, "including", or "is" preceding the recitation of the composition, element or group of elements and vice versa.

Unless the context requires otherwise, throughout the present specification and claims, the word "comprise" and variation thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment is included in at least one embodiment of the present instant invention. Thus, the appearances of the phrases "in one embodiment" in various places throughout this specification are not necessarily all referring to the same embodiment. Furthermore, the particular features, structures, or characteristics may be combined in any suitable.

The present invention relates to a novel and improved formulation of ivermectin cyclodextrin complex into topical pharmaceutical compositions useful for the treatment of inflammatory skin conditions. The topical pharmaceutical composition is suited for administration to humans.

In one of the embodiments the present instant invention describes a new topical solubilized ivermectin pharmaceutical composition which presents comparatively superior pharmaceutical properties than previously known formulations.

In one embodiment of the present invention, the invention provides an ivermectin in a 0.125% to 5% (w/w) concentration and a cyclodextrin. Further, the ivermectin is combined with the cyclodextrin to form an ivermectin-cyclodextrin complex which is solubilized in a Tween80-water solution to a maximum of 30% by weight of solution.

Moreover, in another embodiment of the present invention discloses a formulation of Ivermectin-cyclodextrin complex solubilized in a Tween80-water solution incorporated into lotion or cream or gel base that is highly effective in the treatment of inflammatory skin conditions at a concentration of 0.125% to 5% ivermectin by weight.

Furthermore, in one of the embodiments, the ivermectin according to the invention contains at least 80% of 22,23-dihydroavermectin B1a and less than 20% of 22,23-dihydroavermectin B1b.

The pharmaceutical composition according to the present invention is suited for treating the skin and is in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases. Moreover, the composition is also in the form of suspensions of microspheres or nanospheres or of lipid or polymeric vesicles or of polymeric patches and of hydrogels for controlled release. Furthermore, these compositions for topical application are in anhydrous form.

In an embodiment of the invention, the pharmaceutical compositions according to the invention are in the form of a cream or lotion type, of a gel, or of a solution.

The present invention in an embodiment utilizes an aloe vera gel which increases viscosity by physically stirring and incorporating the ivermectin as it is solubilized.

The compositions of the present invention can be simple gels such as aloe vera gel 98% wherein the solubilized Ivermectin cyclodextrin complex at pH 6.4 is combined into the aloe vera gel for direct application to the skin surface. Equally the dissolved Ivermectin cyclodextrin complex at 30% maximum concentration (0.125% to 5% of Ivermectin (w/w)) can be combined with various skin cream bases as are known in the art but do not need solvent and/335 or alcohol base penetrants and solubilizers for the Ivermectin.

The gel, cream and/or lotion should be free of all other irritants such as parabens, methylparabens, phthalates and all other agents and preservatives known to elicit allergenic or immunogenic reactions.

The Ivermectin cyclodextrin complex being advantageously solubilized within the TWEEN80/water solution to a maximum of 30% by weight of solution can be effectively dispersed within any cream, gel or lotion as are known in the art to be non-irritating to inflamed skin or combined with certain creams such as hydrocortisone creams such that the effective dose of Ivermectin on a w/w basis can be from 0.125% to 5% and more specifically, in some embodiments, to form 0.125% to 5% of the weight of the cream, lotion or gel.

In yet another embodiment, the composition utilizes 100% organic materials such as sunflower oil, aloe vera, coconut oil, oat/milk and/or vitamin E cream base.

In yet another embodiment, the present invention provides the composition for inflammatory skin conditions such as Dermatitis, Psoriasis, and Eczema.

As to the manner of usage and operation of the instant invention, same should be apparent from the above disclosure, and accordingly no further discussion relevant to the manner of usage and operation of the instant invention shall be provided.

Therefore, the foregoing is considered illustrative of only the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The foregoing discussion is illustrative of the invention. However, since many embodiments of the invention can be made without departing from the spirit and scope of the invention, the invention resides wholly in the claims hereinafter appended.

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalence of the claims are to be embraced within their scope. Combinations of any of the methods, systems, and devices described herein-above are also contemplated and within the scope of the disclosed technology.

What is claimed is:

1. A topical ivermectin pharmaceutical composition, comprising: an ivermectin in a 0.125% to 5% (w/w) concentration; and
   a cyclodextrin,
   wherein said ivermectin is complexed with said cyclodextrin to form an ivermectin-cyclodextrin complex solubilized in a polysorbate 80-water solution up to a 30% by weight of said solution;
   wherein said solubilized ivermectin-cyclodextrin complex is combined with an aloe vera gel at pH 6.4 for direct application to skin.

2. The topical ivermectin pharmaceutical composition according to claim 1, wherein said composition is formulated for topical administration.

3. The topical ivermectin pharmaceutical composition according to claim 2, wherein said composition for topical administration is in an anhydrous form.

4. The topical ivermectin pharmaceutical composition according to claim 1, wherein said composition is formulated for the treatment and/or prevention of inflammatory skin conditions.

5. The topical ivermectin pharmaceutical composition according to claim 4, wherein said inflammatory skin conditions comprises of Dermatitis, Psoriasis, and Eczema.

6. The topical ivermectin pharmaceutical composition according to claim 1, wherein said composition is in the form of an ointment, creams, milks, pomades, powders, impregnated pads, syndets, towelettes, gels, sprays, foams, suspensions, lotions, sticks, shampoos or washing bases.

7. The topical ivermectin pharmaceutical composition according to claim 1, wherein said composition provide controlled release and is in the form of a hydrogel and at least one of a microsphere, a nanosphere, a lipid, a polymeric vesicle, or a polymeric patch.

8. The topical ivermectin pharmaceutical composition according to claim 1, wherein said composition is in the form of a cream, lotion, gel, or a solution.

9. The topical ivermectin pharmaceutical composition according to claim 8, wherein said composition is free from irritants selected from a group consisting of parabens, methylparabens, phthalates and all other agents and preservatives that elicit allergenic or immunogenic reactions.

10. The topical ivermectin pharmaceutical composition according to claim 8, wherein said invermectin-cyclodextrin complex is effectively dispersed within said form of cream, lotion or gel or combined with hydrocortisone creams.

11. The topical ivermectin pharmaceutical composition according to claim 1, wherein said invermectin-cyclodextrin complex is non-irritating to inflamed skin.

12. The topical ivermectin pharmaceutical composition according to claim 8, wherein an effective dose of said ivermectin on a w/w basis is, at minimum, from 0.125% to 5% of the weight of said form of cream, lotion or gel.

* * * * *